United States Patent
Kishima

(10) Patent No.: US 10,215,684 B2
(45) Date of Patent: Feb. 26, 2019

(54) FINE PARTICLE DETECTION DEVICE

(71) Applicant: SONY CORPORATION, Tokyo (JP)

(72) Inventor: Koichiro Kishima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/767,767

(22) PCT Filed: Aug. 18, 2016

(86) PCT No.: PCT/JP2016/074159
§ 371 (c)(1),
(2) Date: Apr. 12, 2018

(87) PCT Pub. No.: WO2017/073143
PCT Pub. Date: May 4, 2017

(65) Prior Publication Data
US 2018/0306697 A1 Oct. 25, 2018

(30) Foreign Application Priority Data
Oct. 27, 2015 (JP) .................. 2015-210980

(51) Int. Cl.
*G01N 15/00* (2006.01)
*G01N 15/14* (2006.01)
*G01N 21/64* (2006.01)

(52) U.S. Cl.
CPC ....... *G01N 15/1436* (2013.01); *G01N 21/645* (2013.01)

(58) Field of Classification Search
CPC .......................... G01N 15/1436; G01N 21/645
(Continued)

(56) References Cited

U.S. PATENT DOCUMENTS

2012/0018650 A1* 1/2012 Toishi .................. G01N 15/147
250/458.1
2014/0374630 A1 12/2014 Saiyed et al.

FOREIGN PATENT DOCUMENTS

CN 102346145 A 2/2012
CN 104136922 A 11/2014
(Continued)

OTHER PUBLICATIONS

International Search Report and Written Opinion of PCT Application No. PCT/JP2016/074159, dated Oct. 18, 2016, 7 pages.

*Primary Examiner* — Michael Maskell
(74) *Attorney, Agent, or Firm* — Chip Law Group

(57) ABSTRACT

A fine particle detection device according to the present disclosure includes: a first irradiation portion configured to radiate excitation light to a flow passage in which a fine particle flows to excite fluorescent light from the fine particle; a first separation portion configured to separate the excitation light and the fluorescent light from light that has been radiated to the flow passage by the first irradiation portion; a first detection portion configured to detect the fluorescent light separated by the first separation portion; a second irradiation portion configured to radiate the excitation light separated by the first separation portion to the flow passage to excite the fluorescent light from the fine particle; a second separation portion configured to separate the excitation light and the fluorescent light from light that has been radiated to the flow passage by the second irradiation portion; and a second detection portion configured to detect the fluorescent light separated by the second separation portion.

13 Claims, 11 Drawing Sheets

(58) Field of Classification Search
USPC .................................. 250/458.1, 435, 492.1
See application file for complete search history.

(56) References Cited

FOREIGN PATENT DOCUMENTS

| | | |
|---|---|---|
| EP | 2810063 A1 | 12/2014 |
| JP | 11-087823 A | 3/1999 |
| JP | 2012-026837 A | 2/2012 |
| JP | 2015-512615 A | 4/2015 |
| KR | 10-2014-0124388 A | 10/2014 |
| WO | 2013/114333 A1 | 8/2013 |

* cited by examiner

FINE PARTICLE DETECTION DEVICE

CROSS REFERENCE TO RELATED APPLICATIONS

This application is a U.S. National Phase of International Patent Application No. PCT/JP2016/074159 filed on Aug. 18, 2016, which claims priority benefit of Japanese Patent Application No. JP 2015-210980 filed in the Japan Patent Office on Oct. 27, 2015. Each of the above-referenced applications is hereby incorporated herein by reference in its entirety.

TECHNICAL FIELD

The present disclosure relates to a fine particle detection device.

BACKGROUND ART

Hitherto, for example, Patent Literature 1 below describes a fine particle measurement device that is provided with an optical filter divided into a plurality of areas on an optical path through which light emitted from a fine particle by light irradiation is guided to an optical detector. The optical filter includes a first area having a wavelength selectivity to block reflection light and an unnecessary scattered light component from the fine particle but transmit fluorescence, and a second area arranged at least around the above-mentioned area, having no wavelength selectivity thereby allowing transmission of a necessary scattered light component.

CITATION LIST

Patent Literature

Patent Literature 1: JP 2012-26837A

DISCLOSURE OF INVENTION

Technical Problem

However, a device referred to as a flow cytometer, such as the one described in the above-mentioned Patent Literature, radiates excitation light such as laser light to a fine particle flowing in a flow passage and detects only fluorescent light that has been excited by irradiation of the fine particle and separated from the excitation light not irradiating the fine particle. In this manner, the excitation light not irradiating the fine particle does not contribute to emission of the fluorescent light, thereby causing a problem of lowering the overall utilization efficiency of the excitation light.

Thus, there has been a demand for increasing the utilization efficiency of the excitation light not irradiating the fine particle flowing in the flow passage.

Solution to Problem

According to the present disclosure, there is provided a fine particle detection device including: a first irradiation portion configured to radiate excitation light to a flow passage in which a fine particle flows to excite fluorescent light from the fine particle; a first separation portion configured to separate the excitation light and the fluorescent light from light that has been radiated to the flow passage by the first irradiation portion; a first detection portion configured to detect the fluorescent light separated by the first separation portion; a second irradiation portion configured to radiate the excitation light separated by the first separation portion to the flow passage to excite the fluorescent light from the fine particle; a second separation portion configured to separate the excitation light and the fluorescent light from light that has been radiated to the flow passage by the second irradiation portion; and a second detection portion configured to detect the fluorescent light separated by the second separation portion.

Advantageous Effects of Invention

As described above, according to the present disclosure, it becomes possible to increase the utilization efficiency of the excitation light not irradiating the fine particle flowing in the flow passage.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
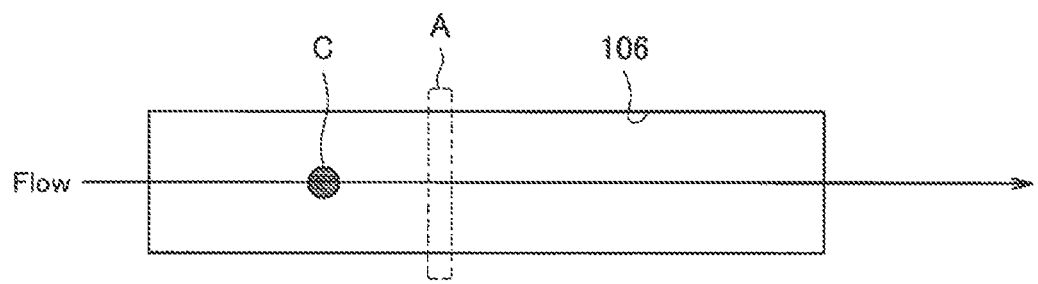
FIG. 1 is a schematic view illustrating a flow passage of a flow cytometer viewed from a radiation direction of laser light.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Underlying techniques
2. Configuration examples of device according to present embodiment

[1. Underlying Techniques]

A flow cytometer is a device that determines characteristics of a cell transmitting through an inside of a flow passage. A cell is labelled in advance with a fluorescent reagent to be evaluated and irradiated with laser light that excites the fluorescent reagent to measure the quantity of fluorescence from the cell. Further, as a means of evaluating the cell, the device generally has a function of estimating a size of the cell by receiving scattered (backscattered or side-scattered) light of the laser radiated to the cell.

The quantity of the fluorescence emitted by irradiating the cell with laser light is proportional to an intensity of the laser light radiated to the cell. However, the intensity of a laser light source is limited, thus the cell is preferably irradiated in a small laser spot to obtain a strong fluorescence signal. Further, there is a demand for using low-output laser to reduce the cost of raw materials of the device. Considering such an aspect as well, the cell is preferably irradiated in a small laser spot to obtain a strong fluorescence signal.

FIG. 1 is a schematic view illustrating a flow passage 106 of a flow cytometer viewed from a radiation direction of laser light. In the flow cytometer, conditions of the flow passage passing through fluorescence are set to create a laminar flow. However, cells C passing through the flow passage vary in size. Further, if sheath fluid, which is supplied to cause the cell C to run in the center of the flow, loses its balance, the cell C may be prevented from flowing in the center of the flow passage. Further, in the case where the device in which the flow passage 106 is arranged is detachably formed, or the like, an installing position of the flow passage 106 may vary relative to a radiation position of the laser light. Thus, an irradiation area A of the laser light radiated to the cell C is generally formed into a beam shape extended in a direction perpendicular to the flow of the flow passage 106 as shown in FIG. 1. Accordingly, a shape of the beam spot (a shape of the irradiation area A) is optimized by taking into consideration a room for reducing the cost of a liquid-feed control system of the sheath fluid, margins of the accuracy of the flow passage 106 and the accuracy of its installation position, the cost of the laser light source, and the like.

Figure 2:
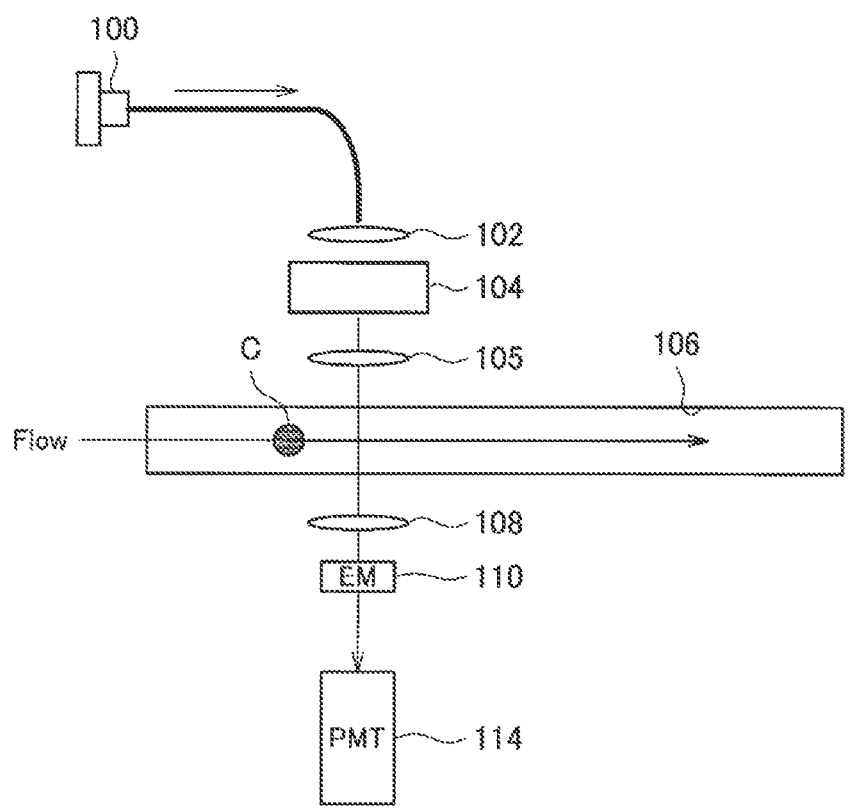
FIG. 2 is a schematic view illustrating a basic configuration of the flow cyto.

FIG. 2 is a schematic view illustrating a basic configuration of the flow cyto. In FIG. 2, the laser light emitted from a laser light source 100 is transmitted through a lens 102, shaped by a beam shaping portion 104, condensed by a lens 105, and radiated to the cell C flowing through the flow passage 106. The fluorescence emitted by the laser light that is radiated to the cell C is condensed by a lens 108 and enters an emission filter (EM) 110. The emission filter 110 absorbs the laser light (excitation light) that is radiated to the cell and transmits the fluorescence (emission light) that is emitted from the cell. The fluorescence that has transmitted through the emission filter 110 is radiated to and detected by a PMT (Photomultiplier Tube) functioning as a high-sensitivity light receiving element 114.

In the configuration shown in FIG. 2, the laser light radiated to the flow passage 106 has an extended shape as shown in FIG. 1. Thus, the proportion of the laser light that is radiated to the cell C, thereby contributing to fluorescent emission, is low in the entire laser light radiated to the flow passage 106. Further, most of the laser light radiated to the flow passage 106 is absorbed by the emission filter 110 without irradiating the cell C. Thus, the utilization efficiency of the laser light is low in the configuration shown in FIG. 2.

As described above, the beam spot in the flow cytometer is formed in an extended shape as shown in FIG. 1 in consideration of evaluating larger cell C, ensuring a room for reducing the cost of the liquid-feed control system of the sheath fluid, ensuring margins of the accuracy of the flow passage 106 and the accuracy of its installation position, reducing the cost of the laser light source, or the like. As a result, in the entire laser light radiated to the flow passage 106, most of the laser light radiated to the flow passage 106 is absorbed by the emission filter 110 without irradiating the cell C. The present embodiment is intended to increase the utilization efficiency of the laser light (excitation light) radiated to the cell. A detailed description is provided below.

[2. Configuration Examples of Device According to Present Embodiment]

Figure 3:
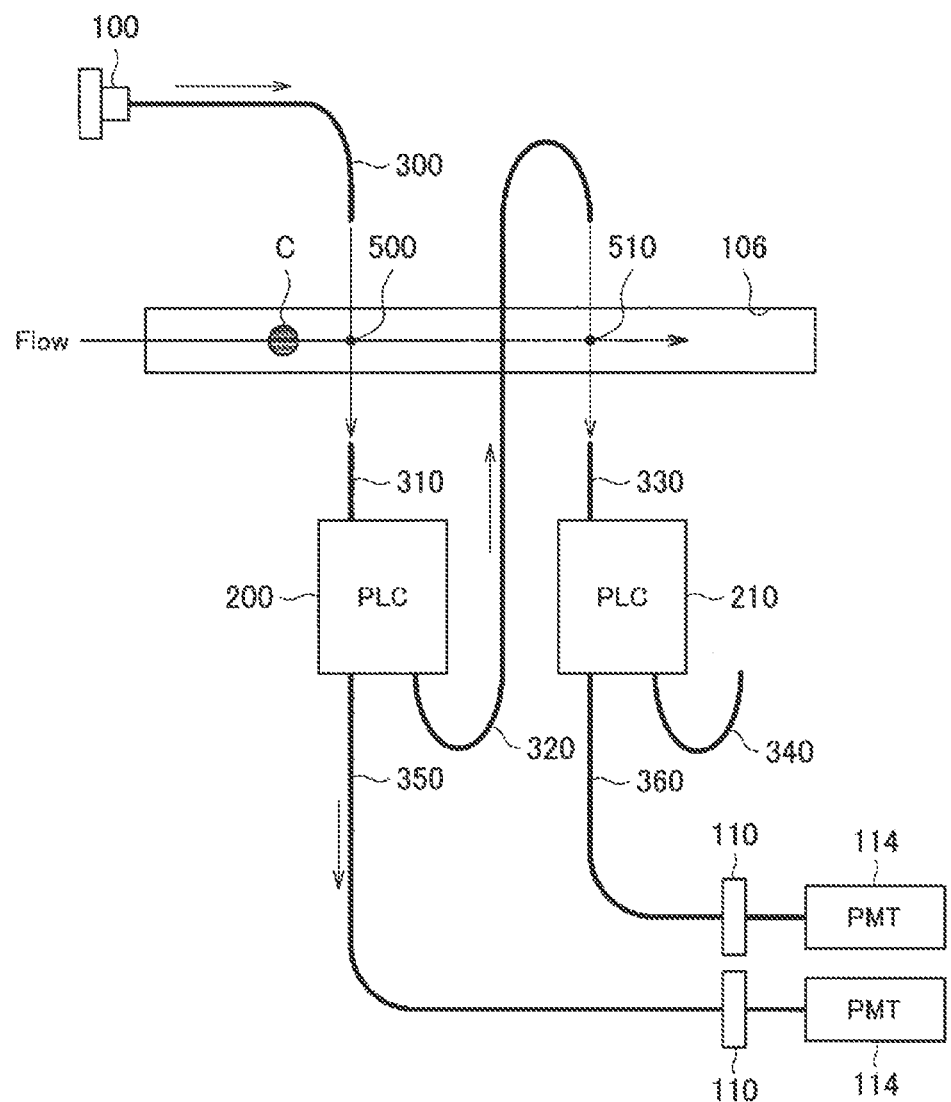
FIG. 3 is a schematic view illustrating an example of an analyzer, according to the present embodiment, for increasing the utilization efficiency of the laser light (excitation light) to be radiated to a cell.

FIG. 3 is a schematic view illustrating an example of a fine particle observation device 1000, according to the present embodiment, for increasing the utilization efficiency of the laser light (excitation light) radiated to the cell. In addition to the configuration in FIG. 2, this device is provided with so-called PLC (Planar Lightwave Circuit) type spectroscopic elements 200 and 210, in each of which an optical waveguide is formed in a substrate made of an optical material, in a state prior to the emission filter (EM) 110. Note that the lenses 102, 105, and 108, and the beam shaping portion 104 are omitted in FIG. 3.

Figure 4:
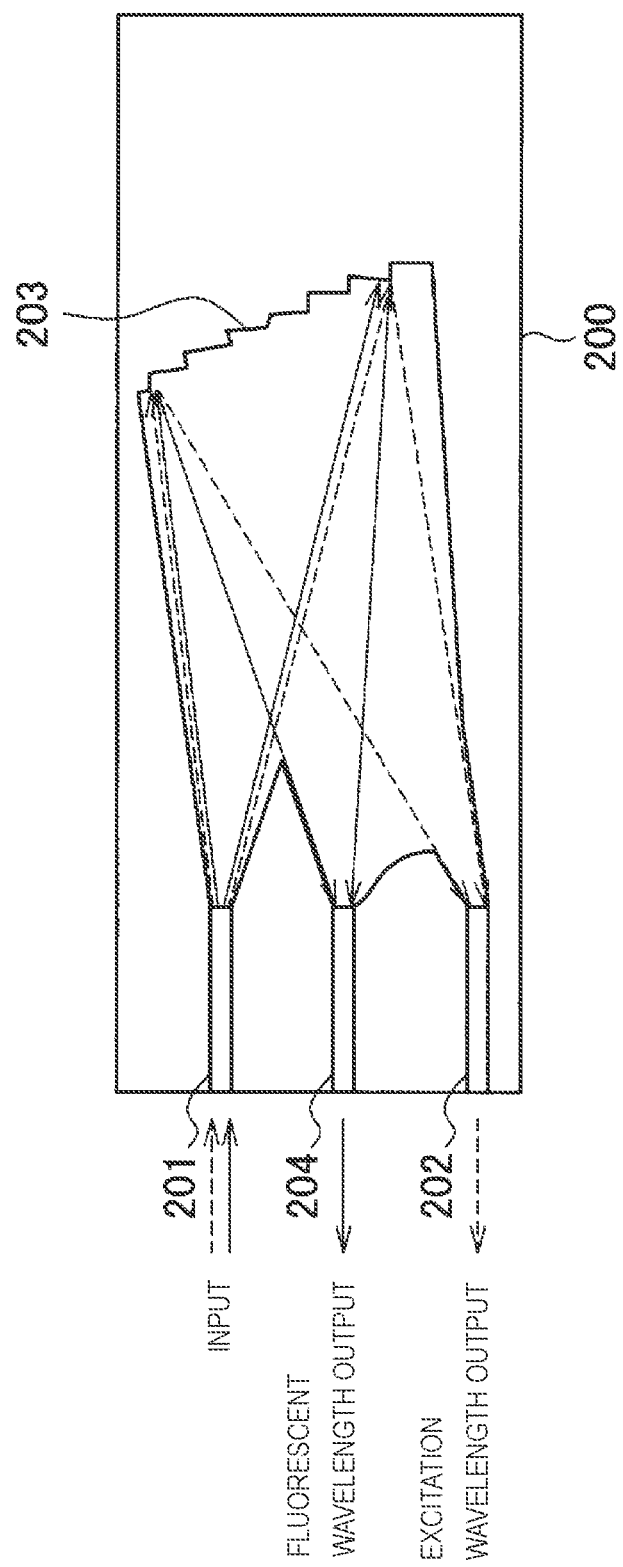
FIG. 4 is a schematic view illustrating a configuration example of a spectroscopic element.

FIG. 4 is a schematic view illustrating a configuration example of the spectroscopic element 200. The spectroscopic element 200 receives mixed light of the excitation light and the fluorescent light as input light from an input portion 201 and separates the mixed light into the excitation light and the fluorescent light by a grating structure 203 formed in the optical waveguide to output. In this configuration, the excitation light is outputted from an excitation light output portion (an excitation light output port) 202, while the fluorescent light is outputted from a fluorescent light output portion (a fluorescent light output port) 204.

In FIG. 3, the laser light emitted from the laser light source 100 is guided to the flow passage 106 by an optical waveguide (an optical fiber) 300. The excitation light radiated to the cell C in the flow passage 106 may change its polarization direction, thus it is difficult to separate completely such excitation light by the spectroscopic element 200. However, the excitation light not radiated to the cell C in the flow passage 106 undergoes little change in the polarization direction or the like and maintains characteristics at the time of transmitting through the lens 105 arranged in front of the flow passage 106 at a considerably high level. Thus, the excitation light is guided to the spectroscopic element 200 shown in FIG. 4 by an optical waveguide 310 and then effectively guided to the excitation light output portion 202. After that, the excitation light is directly guided to an optical waveguide 320 in the case where the optical waveguide 320 is arranged to the excitation light output portion 202 of the spectroscopic element 200. Note that the above-mentioned optical waveguide 300, lens 102, beam shaping portion 104, lens 105, and lens 108 are collectively referred to as a first irradiation portion of the excitation light.

Further, the fluorescent light is guided to the fluorescent light output portion 204 of the spectroscopic element 200 and then guided to an optical waveguide 350 to enter the emission filter (EM) 110. The fluorescence that has transmitted through the emission filter 110 is radiated to and detected by the PMT functioning as the high-sensitivity light receiving element 114.

In a configuration shown in FIG. 4, the excitation laser light guided to the optical waveguide 320 by the spectroscopic element 200 is reused by re-guiding the excitation laser light from the optical waveguide 320 to the flow passage 106. In this configuration, the laser light guided to the excitation light output portion 202 is guided to the optical waveguide 320 to irradiate the cell C flowing in the flow passage 106 again with the laser light in a similar manner to the case where the laser outputted from the laser light source 100 for outputting excitation laser is guided to the optical waveguide 300. That is, in addition to an irradiation portion (a first detection portion (a Detection Point 1) 500) formed on the flow passage 106 by the laser outputted from the laser light source 100 for outputting excitation laser, a new irradiation portion (a second detection portion (a Detection Point 2) 510) can be formed on the flow passage 106 by the excitation laser light that is separated from the fluorescent light by the spectroscopic elements 200 and re-guided to the optical waveguide 320, so that the cell can be evaluated by two detection portions 500 and 510.

Note that, although not illustrated, the lenses 102, 105, and 108, and the beam shaping portion 104 are also provided in the second detection portion 510. Note that the above-mentioned optical waveguide 320, lens 102, beam shaping portion 104, lens 105, and lens 108 are collectively referred to as a second irradiation portion of the excitation light.

Further, also in the second detection portion 510, the excitation light not radiated to the cell C in the flow passage 106 undergoes little change in the polarization direction or the like and maintains characteristics at the time of transmitting through the lens 105 arranged in a stage prior to the flow passage 106 at a high level. Thus, the excitation light is guided to the second spectroscopic element 210 by an optical waveguide 330 and then effectively guided to an excitation light output portion 212 by the second spectroscopic element 210 as is the case with the spectroscopic element 200. Then, the excitation light can be directly guided to an optical waveguide 340 to irradiate the flow passage 106 again in the case where the optical waveguide 340 is arranged to the excitation light output portion 212 of the spectroscopic element 210. In this manner, the utilization efficiency of the laser light radiated to the cell C can be further increased.

Further, the fluorescent light from the second detection portion 510 is guided to a fluorescent light output portion 214 of the second spectroscopic element 210 and then guided to an optical waveguide 360 to enter the emission filter (EM) 110. The fluorescence that has transmitted through the emission filter 110 is radiated to and detected by the PMT functioning as the high-sensitivity light receiving element 114.

Figure 5:
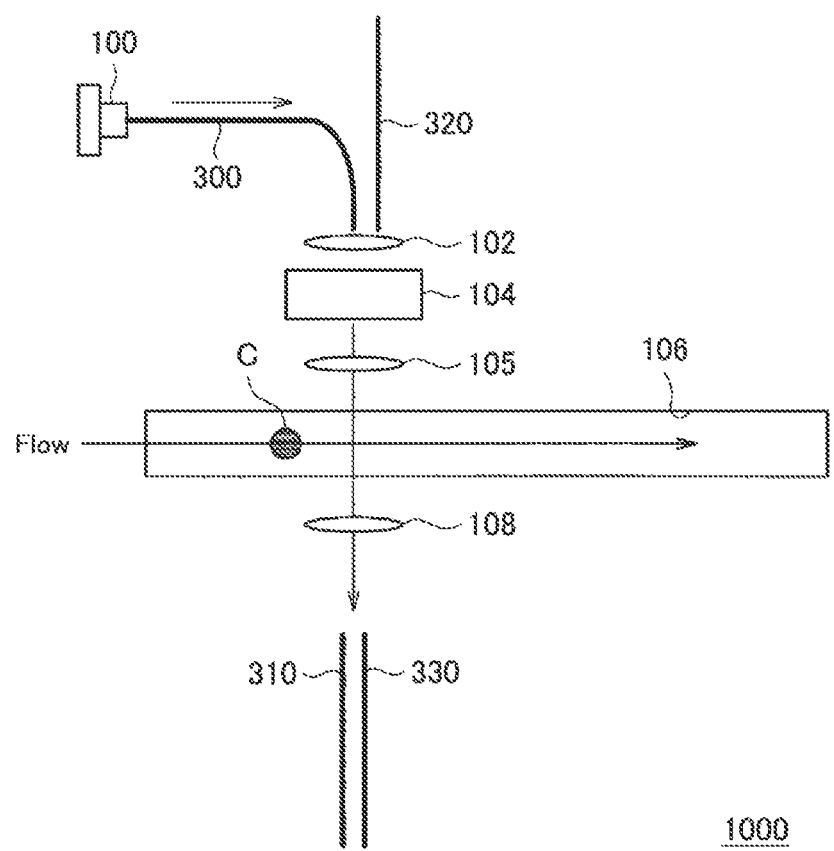
FIG. 5 is a schematic view illustrating an example in which lenses and a beam shaping portion are made common to two detection portions.

Further, in FIG. 3, an optical fiber core without coating is used for the optical waveguide 300 and the optical waveguide 320, as well as for the optical waveguide 310 and the optical waveguide 330, so that positions of their output ends or input ends can be brought close to each other. As shown in FIG. 5, such a configuration allows two detection portions 500 and 510 to use, in common, the lens 102, the beam shaping portion 104, which is an optical system for extending a shape of a beam radiated to the flow passage 106, the lens 105 for forming a spot on the flow passage 106, and the lens 108 for condensing the fluorescent light emitted from the cell C or the laser light (excitation light) radiated to the flow passage 106. This can simplify the configuration and reduce the number of components, thereby enabling to reduce the manufacturing cost.

Figure 6:
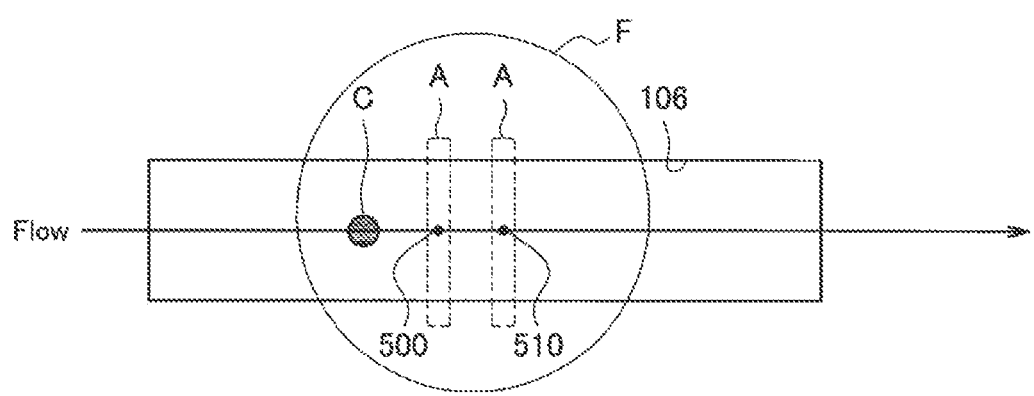
FIG. 6 is a schematic view illustrating a relationship between positions of spots on the flow passage and a visual field of a lens.

FIG. 6 is a schematic view illustrating a relationship between positions of the spots on the flow passage 106 and a visual field of a lens, viewed from a radiation direction of the laser. As described above, on the flow passage 106, the radiated beam is extended in a direction perpendicular to a flow direction of the flow passage 106. On the other hand, a plurality of beams (the first and second detection portions 500 and 510) are arranged in a direction parallel to the low direction of the flow passage 106. As shown in FIG. 6, a visual field F of a lens used in the case where only the first detection portion 510 is configured on the flow passage 106 is designed so as to cover the extended direction of the beam in the irradiation area A, thus it is possible to further arrange an additional beam irradiation area A of substantially the same size in the flow direction of the flow passage 106.

Figure 7:
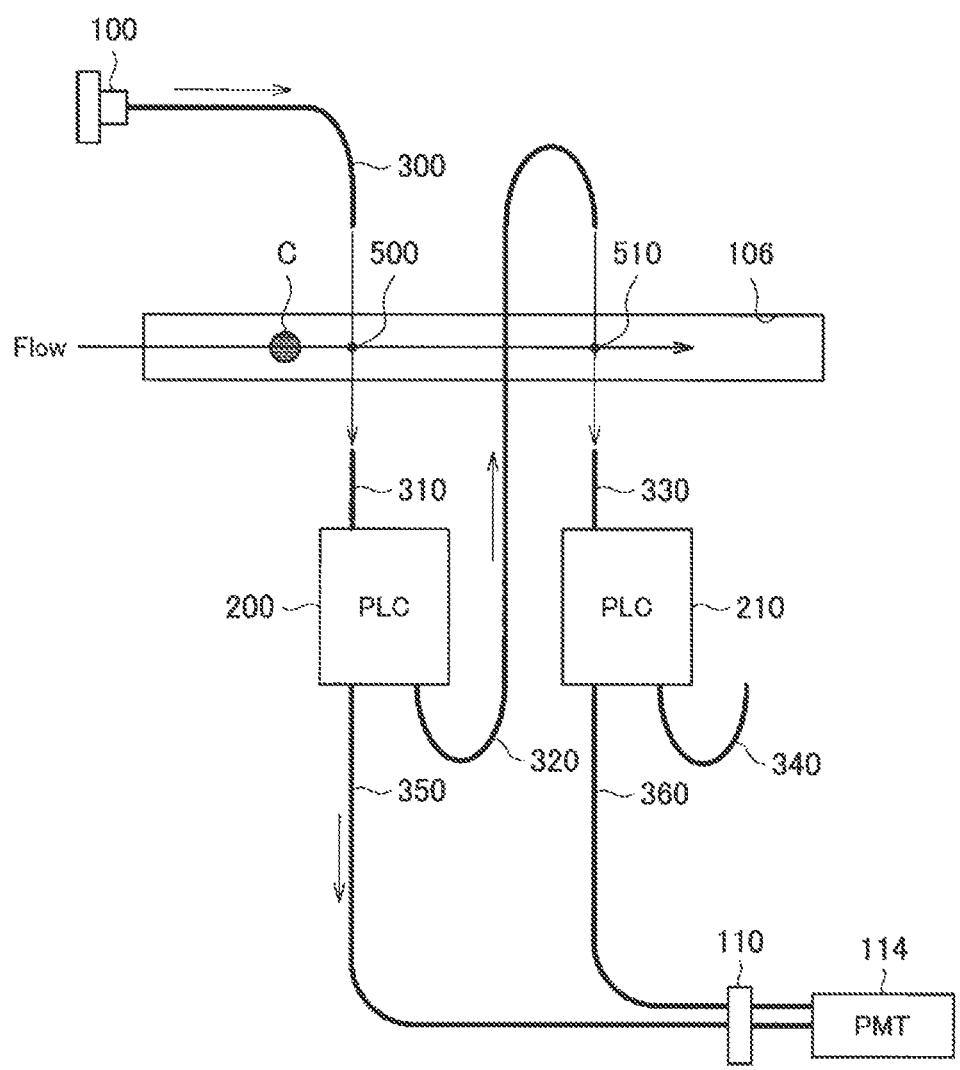
FIG. 7 is a schematic view illustrating an example in which an emission filter and a high-sensitivity light receiving element are made common to a first detection portion and a second detection portion.

FIG. 7 shows an example in which the emission filter 110 and the high-sensitivity light receiving element 114 are made common to the first detection portion 500 and the second detection portion 510. As described above, the optical fiber core without coating or the like is used for the optical waveguide 300 and the optical waveguide 320, as well as for the optical waveguide 310 and the optical waveguide 330, so that the light input ends or the light output ends can be brought close to each other. Thus, in addition to the lenses 102, 105, and 108, and the beam shaping portion 104, the emission filter 110 and the high-sensitivity light receiving element 114 can be used in common. Note that, instead of using the optical fiber core without coating, a ribbon fiber in which a plurality of fiber cores are arranged side by side can be used. According to a configuration shown in FIG. 7, the same fine particle can be detected by both the first detection portion 500 and the second detection portion 510, making it possible to obtain a detection signal practically in a double amount and significantly improve the detection accuracy of the fluorescent light. In other words, according to the configuration shown in FIG. 7, it is possible to obtain the detection signal of the fluorescent light at the level equivalent to the case where an output of the light source 100 is doubled. Such a configuration makes it possible to obtain an S/N ratio at the level equivalent to the case where the output of the light source 100 is doubled without increasing the manufacturing cost.

Figure 8:
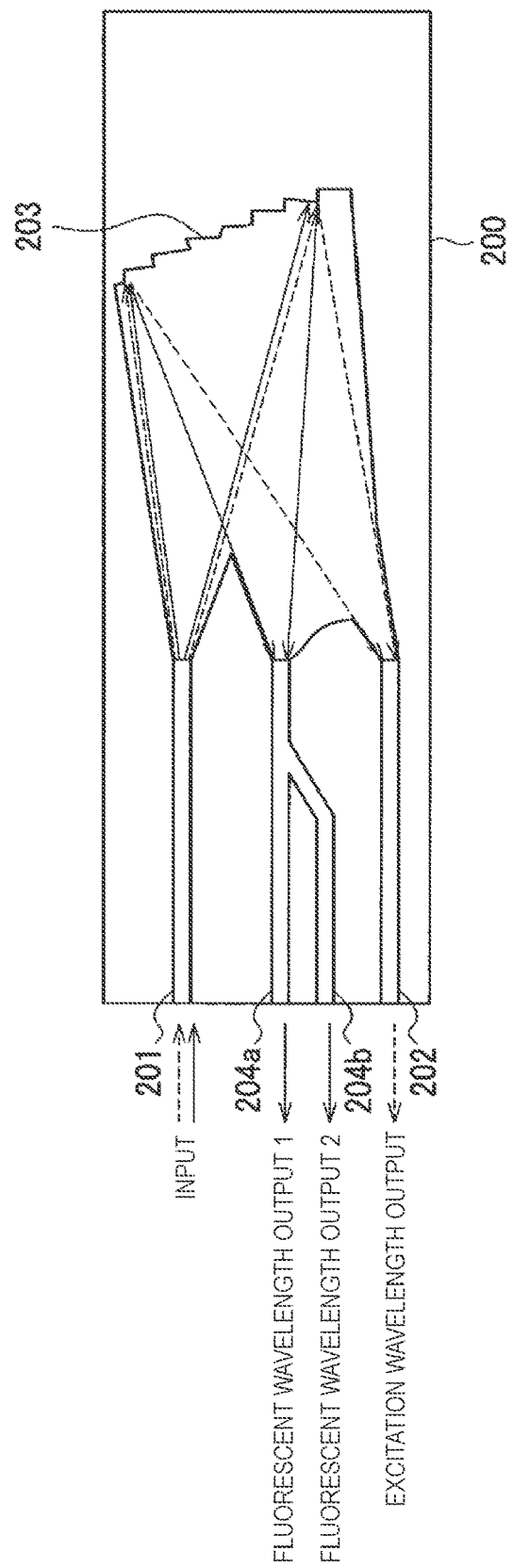
FIG. 8 is a schematic view illustrating the spectroscopic element that is configured to separate fluorescence, which is guided through an optical waveguide, into two fluorescent light output portions.

Further, as shown in FIG. 8, the PLC-type spectroscopic element 200 can achieve a configuration in which the fluorescence to be guided to the optical waveguides 350 is divided into two fluorescent light output portions 204a and 204b with an extremely narrow space. Thus, signal light can be guided to the two fluorescent light output portions 204a and 204b at a specified ratio. Similarly, the fluorescent light can be divided into two fluorescent light output portions 214a and 214b by the second spectroscopic element 210. Thus, the configurations shown in FIG. 3 and FIG. 7 can achieve optical systems shown in FIG. 9 and FIG. 10 by guiding the light divided at the fluorescent wavelength output ports to a PD (Photo Diode) 114a and an MPPC (Multi-Pixel Photon Counter) 114b, both functioning as the high-sensitivity light receiving element 114. In such a configuration, the MPPC 114b has characteristics that can detect weak light, but relatively barely secure a dynamic range. On the other hand, the PD 114a has characteristics that can secure a dynamic range, but relatively barely detect weak light. The PMT can detect weak light and secure a dynamic range, but is relatively more expensive to use. Thus, according to the configurations shown in FIG. 9 and FIG. 10, roles can be shared by the MPPC 114*b* detecting weak light and the PD 114*a* detecting strong light by dividing the quantity of the fluorescent light accordingly.

Figure 9:
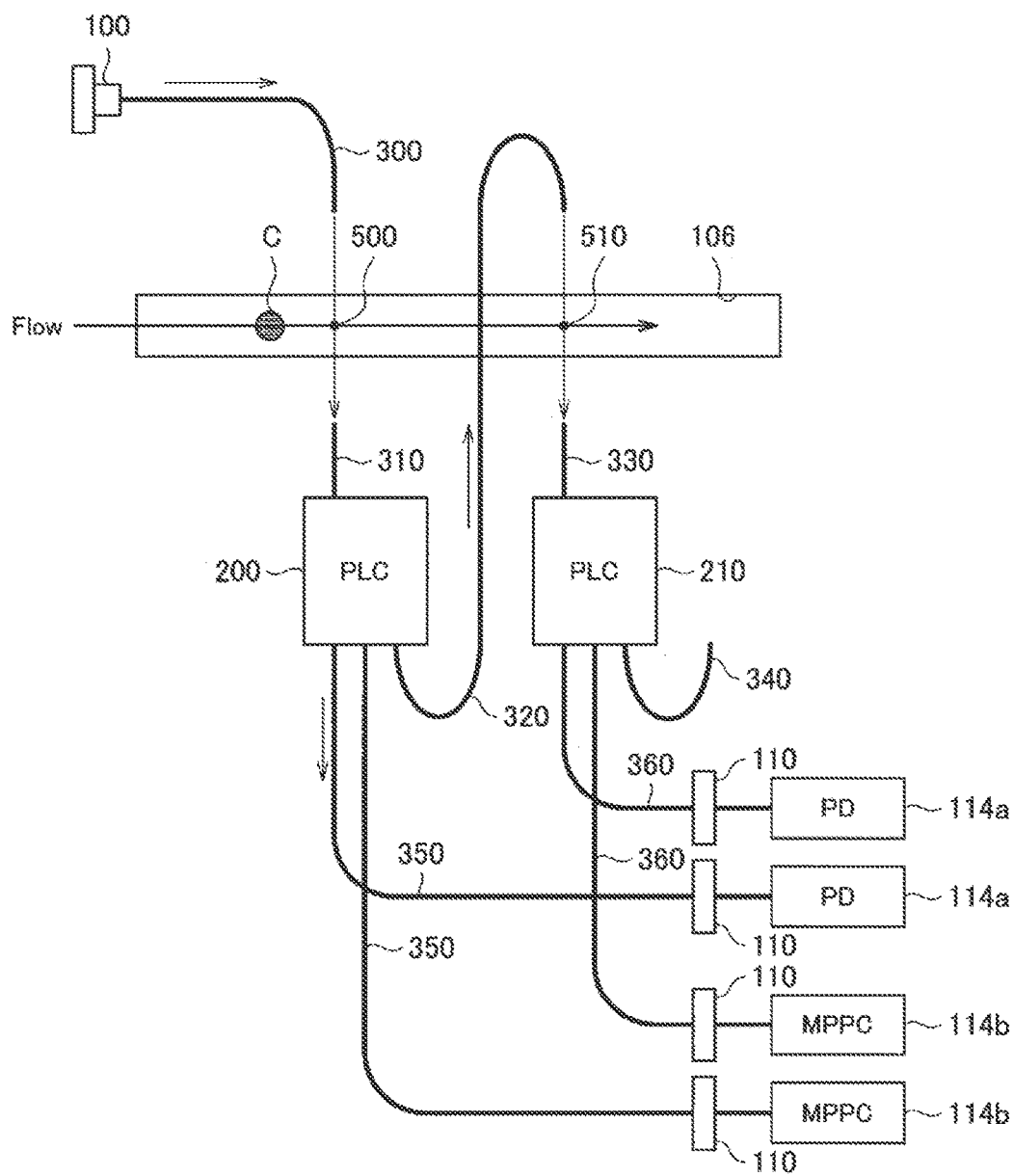
FIG. 9 is a schematic view illustrating an example in which light at fluorescent wavelength output ports is separated into high-sensitivity light receiving elements, PD and MPPC.
Figure 10:
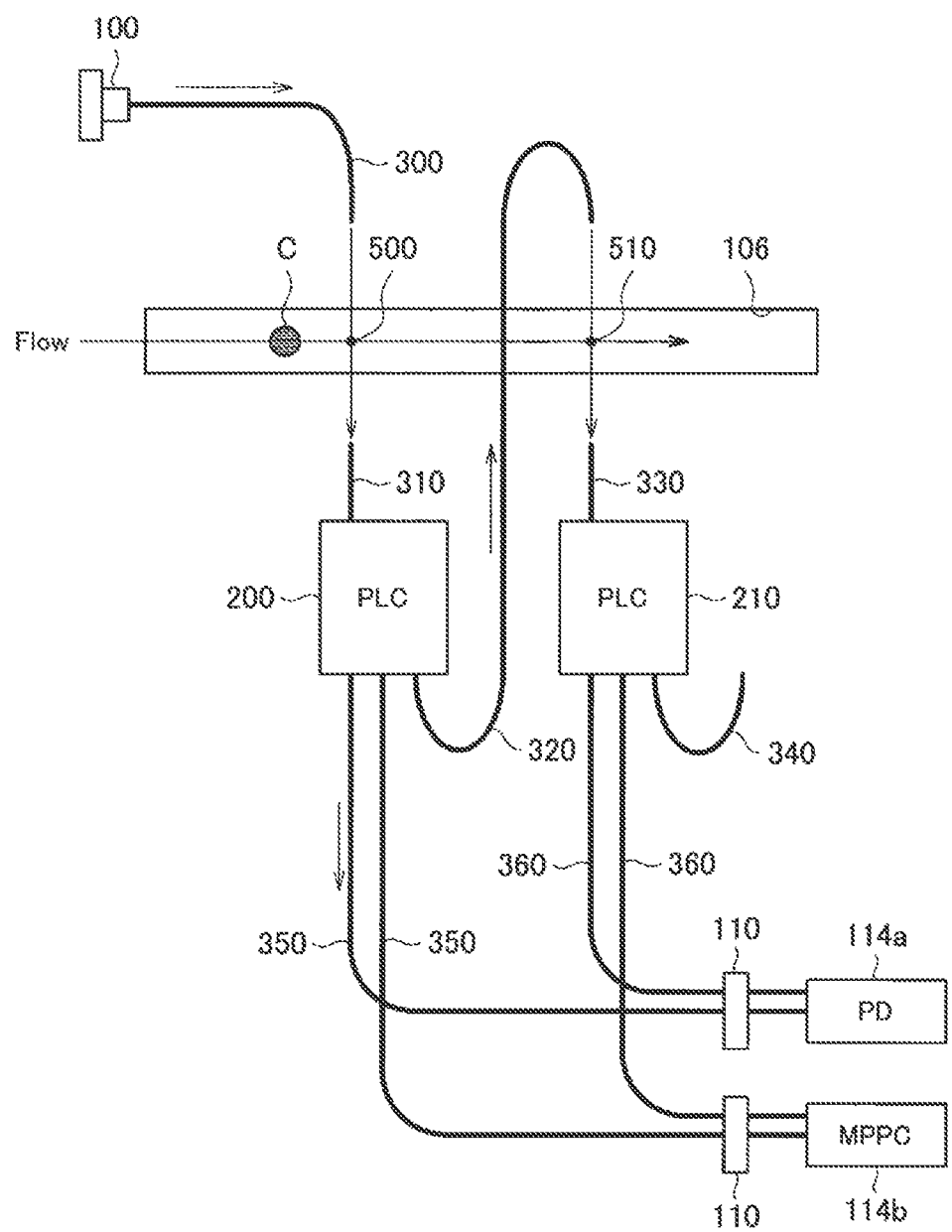
FIG. 10 is a schematic view illustrating an example in which the light at fluorescent wavelength output ports is separated into the high-sensitivity light receiving elements, PD and MPPC.

According to configuration examples shown in FIG. 9 and FIG. 10, evaluation performed by the first detection portion 500 and the second detection portion 510 can be made common. The flow cytometry device described herein generally has a processing capacity of about $2 \times 10^5$ events per second. Each event represents the number of cells to be processed. Further, a standard flow rate in the flow passage 106 is about 10 to 30 m/s. That is, about $2 \times 10^5$ cells are flowing in the fluid flowing at 20 m/s, meaning that consecutive cells flow at intervals of about 100 µm. As shown in the present embodiment, in the case where the excitation light having passed through the first detection portion 500 is reused for the second detection portion 510, assuming that a length of the optical path (including the optical fiber portions) between the first detection portion 500 and the second detection portion 510 is, for example, about 50 cm to 100 cm, light that has passed through the first detection portion 500 reaches the second detection portion 510 after 150 to 300 ps. The cell C flowing at 20 m/s can only move the distance of about 0.003 µm to 0.006 µm in the flow passage 106 during the time period of 150 ps to 300 ps. Thus, it can be assumed that detections by the first detection portion 500 and the second detection portion 510 are performed almost simultaneously. Therefore, it is possible to evaluate the same cell without having a contamination signal from other cells by making the interval between the first detection portion 500 and the second detection portion 510 shorter than the interval of the consecutive cells C in the flow passage 106, more preferably, by making the interval between the first detection portion 500 and the second detection portion 510 half or less than the interval of the consecutive cells C in the flow passage 106. In this manner, as described above, it becomes possible to obtain the detection signal at the level equivalent to the case where the output of the light source 100 is doubled and improve the S/N ratio without increasing the manufacturing cost.

Figure 11:
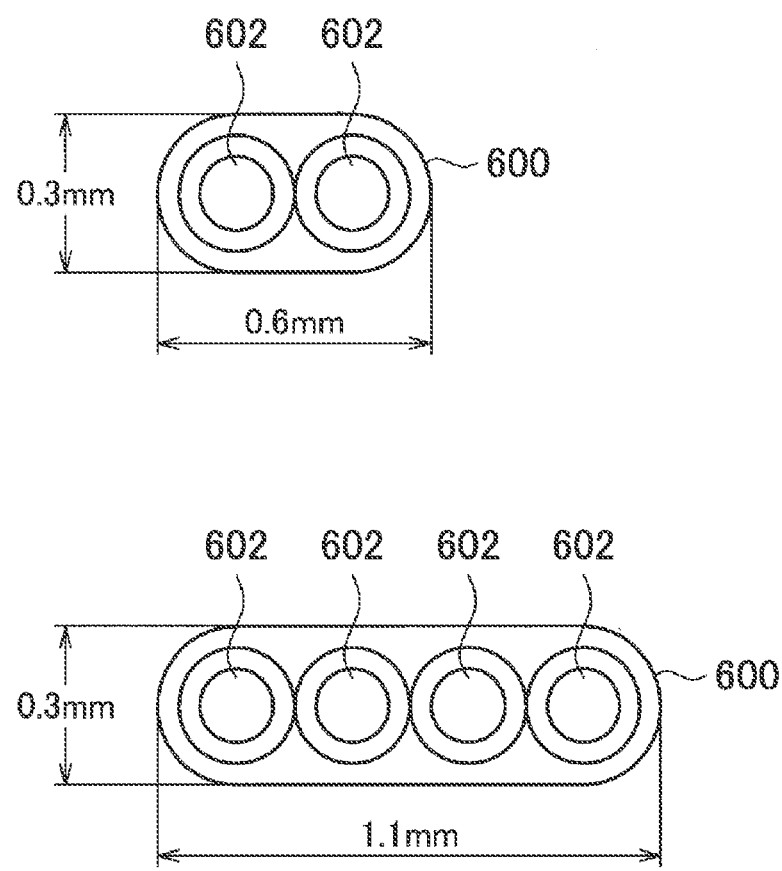
FIG. 11 is a schematic view illustrating examples of a ribbon fiber.

As described above, the ribbon fiber in which a plurality of fiber cores are arranged side by side can be used as the optical waveguide 300 and the optical waveguide 320, as well as as the optical waveguide 310 and the optical waveguide 330. FIG. 11 is a schematic view illustrating examples of the ribbon fiber, specifically, cross sections of the fibers. A ribbon fiber 600 is configured by arranging a plurality of fiber cores 602 side by side. As a ribbon fiber 600 having such a configuration, for example, an optical fiber ribbon manufactured by Sumitomo Electric Industries, Ltd. can be used.

Figure 12:
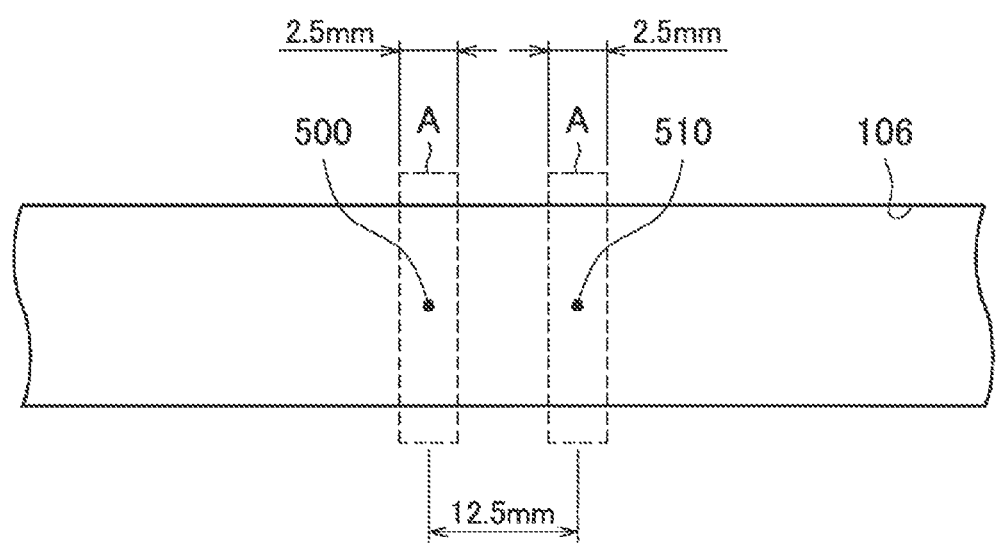
FIG. 12 is a schematic view illustrating an interval between the first detection portion and the second detection portion and a width of an irradiation area A in a flow direction.

For example, in the case where the ribbon fibers 600 are used at an irradiation side and a light receiving side, intervals of the optical fiber cores 602 are, as an example, about 250 µm. If the laser light is formed using the lens 105 having 20-times magnification, the intervals of the fibers are converted from 250 µm to 12.5 µm. As a result, as shown in FIG. 12, the interval between the first detection portion 500 and the second detection portion 510 becomes 12.5 µm. Further, if a width of the irradiation area A in the flow direction is 10 µm after the laser light is shaped by the beam shaping portion 104, the width of the irradiation area A in the flow direction is converted to 2.5 µm after the laser light passes through the lens 105.

Here, the flow cytometer having a relatively high-speed processing capacity is operated at about 50,000 cells/sec under the flow rate of about 20 m/s. Further, the interval of the consecutive cells is about 400 µm. The time when the cell passes through the irradiation area A (a window) having a 10 µm distance is about 0.5 µs. This value is converted into frequency of about 2 MHz.

To measure one cell by the two detection portions 500 and 501 according to the present embodiment, it is preferable that the two detection portions 500 and 501 are sufficiently close to each other as compared to the interval of the consecutive cells. In an example shown in FIG. 12, a total length between the two detection portions 500 and 501 in the flow direction is 22.5 µm (=10+10+2.5). The total length of 22.5 µm is sufficiently short as compared to the interval of the consecutive cells of 400 µm, thus the detection sensitivity of one cell C can be surely increased by the two detection portions 500 and 501 without having contamination of a detection signal from other cell.

Further, the time when the cell passes through the length of 22.5 µm is 1.125 µs and this value is converted into a frequency of about 888 kHz. A signal of 888 kHz obtained when the cell passes through the two detection portions 500 and 501 and a signal of 2 MHz obtained when the cell passes through one of the detection portions can be optically received and recognized as a signal having substantially the same speed by the PMB owing to its characteristics. For example, a general-purpose PMT having a rise time of 1.3 ns and a transit time of 5.8 ns has the same time characteristics between 888 kHz and 2 MHz. Thus, the fluorescent light outputted from one cell can be received by the two detection portions 500 and 501.

As described above, according to the present embodiment, it becomes possible to increase the utilization efficiency of the laser light (excitation light) radiated to the cell by separating the laser light (excitation light) by the spectroscopic element 200 and re-guiding it to the flow passage 106. This allows the first detection portion 500 and the second detection portion 510 to use, in common, the high-sensitivity light receiving element 114 for detecting the fluorescent light, thereby making it possible to improve the S/N ratio of the detection signal of the fluorescent light without increasing the manufacturing cost. Further, a laser light source with lower output power can be used. Moreover, even when measuring the cell having a conventional size, a room for reducing the cost of the liquid-feed control system of the sheath fluid and margins of the accuracy of a flow passage chip and the accuracy of its installation can be ensured in a larger range.

Further, in the case where a laser light source with conventional output power is used, a higher detection signal can be obtained. Also in this case, it is possible to measure the cell having a conventional size while ensuring a room for reducing the cost of the liquid-feed control system of the sheath fluid and margins of the accuracy of the flow passage chip and the accuracy of its installation in a larger range.

Further, positions of light used for forming a plurality of detection spots can be arranged in proximity, thus a beam shaping means, a condenser lens, an emission filter, a high-sensitivity detector, and the like can be used in common, making it possible to improve a function without increasing the manufacturing cost of the system configuration.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A fine particle detection device including:

a first irradiation portion configured to radiate excitation light to a flow passage in which a fine particle flows to excite fluorescent light from the fine particle;

a first separation portion configured to separate the excitation light and the fluorescent light from light that has been radiated to the flow passage by the first irradiation portion;

a first detection portion configured to detect the fluorescent light separated by the first separation portion;

a second irradiation portion configured to radiate the excitation light separated by the first separation portion to the flow passage to excite the fluorescent light from the fine particle;

a second separation portion configured to separate the excitation light and the fluorescent light from light that has been radiated to the flow passage by the second irradiation portion; and a second detection portion configured to detect the fluorescent light separated by the second separation portion.

(2)

The fine particle detection device according to (1), including:

a lens configured to refract the excitation light to be radiated to the flow passage by the first irradiation portion or the second irradiation portion or the light that has been radiated to the flow passage by the first irradiation portion or the second irradiation portion, in which the lens is common to the first irradiation portion and the second irradiation portion.

(3)

The fine particle detection device according to (1), in which the first irradiation portion or the second irradiation portion includes a shaping portion configured to shape the excitation light to be radiated to the flow passage, and the shaping portion is common to the first irradiation portion and the second irradiation portion.

(4)

The fine particle detection device according to (1), in which the first detection portion and the second detection portion are configured as a common detection portion.

(5)

The fine particle detection device according to (1), in which the first separation portion includes a plurality of fluorescent light output portions configured to separate and output the fluorescent light, and the first detection portion includes a plurality of detection portions that have different characteristics, and detect the fluorescent light outputted from the plurality of the fluorescent light output portions.

(6)

The fine particle detection device according to (1), in which the second separation portion includes a plurality of fluorescent light output portions configured to separate and output the fluorescent light, and the second detection portion includes a plurality of detection portions that have different characteristics, and detect the fluorescent light outputted from the plurality of the fluorescent light output portions.

(7)

The fine particle detection device according to (1), in which the first separation portion includes a plurality of fluorescent light output portions configured to separate and output the fluorescent light, the first detection portion includes a plurality of detection portions configured to detect the fluorescent light outputted from the plurality of the fluorescent light output portions, the second separation portion includes a plurality of fluorescent light output portions configured to separate and output the fluorescent light, the second detection portion includes a plurality of detection portions configured to detect the fluorescent light outputted from the plurality of the fluorescent light output portions, and at least one of the plurality of the detection portions included in the first detection portion and at least one of the plurality of the detection portions included in the second detection portion are configured as a common detection portion.

(8)

The fine particle detection device according to (1), in which the first irradiation portion and the second irradiation portion each include an optical waveguide for radiating the excitation light to the flow passage.

(9)

The fine particle detection device according to (8), in which the optical waveguide of the first irradiation portion and the optical waveguide of the second irradiation portion are arranged adjacent to each other in a flow direction of the fine particle in the flow passage.

(10)

The fine particle detection device according to (8), in which the optical waveguide of the first irradiation portion and the optical waveguide of the second irradiation portion are configured as an integrated optical fiber ribbon.

(11)

The fine particle detection device according to (1), in which the first irradiation portion includes an optical waveguide for transmitting light that has been radiated to the flow passage to the first separation portion, and the second irradiation portion includes an optical waveguide for transmitting light that has been radiated to the flow passage to the second separation portion.

(12)

The fine particle detection device according to (11), in which the optical waveguide of the first irradiation portion and the optical waveguide of the second irradiation portion are arranged adjacent to each other in a flow direction of the fine particle in the flow passage.

(13)

The fine particle detection device according to (12), in which the optical waveguide of the first irradiation portion and the optical waveguide of the second irradiation portion are configured as an integrated optical fiber ribbon.

REFERENCE SIGNS LIST

100 laser light source
114 high-sensitivity light receiving element 200, 210 spectroscopic elements
300, 320 optical waveguides

The invention claimed is:

1. A fine particle detection device, comprising:
   a first irradiation portion configured to radiate excitation light to a flow passage in which a fine particle flows to excite fluorescent light from the fine particle;
   a first separation portion configured to separate the excitation light and the fluorescent light from first light that has been radiated to the flow passage by the first irradiation portion;
   a first detection portion configured to detect the fluorescent light separated by the first separation portion;
   a second irradiation portion configured to radiate the excitation light separated by the first separation portion to the flow passage to excite the fluorescent light from the fine particle;
   a second separation portion configured to separate the excitation light and the fluorescent light from second light that has been radiated to the flow passage by the second irradiation portion; and
   a second detection portion configured to detect the fluorescent light separated by the second separation portion.

2. The fine particle detection device according to claim 1, comprising:
   a lens configured to refract one of:
      the excitation light to be radiated to the flow passage by one of the first irradiation portion or the second irradiation portion,
      the first light that has been radiated to the flow passage by the first irradiation portion, or
      the second light that has been radiated to the flow passage by the second irradiation portion, wherein the lens is common to the first irradiation portion and the second irradiation portion.

3. The fine particle detection device according to claim 1, wherein
   at least one of the first irradiation portion or the second irradiation portion includes a shaping portion configured to shape the excitation light to be radiated to the flow passage, and
   the shaping portion is common to the first irradiation portion and the second irradiation portion.

4. The fine particle detection device according to claim 1, wherein the first detection portion and the second detection portion are configured as a common detection portion.

5. The fine particle detection device according to claim 1, wherein
   the first separation portion includes a plurality of fluorescent light output portions configured to separate and output the fluorescent light,
   the first detection portion includes a plurality of detection portions that has different characteristics, and the plurality of detection portions is configured to detect the fluorescent light outputted from the plurality of fluorescent light output portions.

6. The fine particle detection device according to claim 1, wherein
   the second separation portion includes a plurality of fluorescent light output portions configured to separate and output the fluorescent light,
   the second detection portion includes a plurality of detection portions that has different characteristics, and the plurality of detection portions is configured to detect the fluorescent light outputted from the plurality of fluorescent light output portions.

7. The fine particle detection device according to claim 1, wherein
   the first separation portion includes a plurality of first fluorescent light output portions configured to separate and output the fluorescent light,
   the first detection portion includes a plurality of first detection portions configured to detect the fluorescent light outputted from the plurality of first fluorescent light output portions,
   the second separation portion includes a plurality of second fluorescent light output portions configured to separate and output the fluorescent light,
   the second detection portion includes a plurality of second detection portions configured to detect the fluorescent light outputted from the plurality of second fluorescent light output portions, and
   at least one of the plurality of first detection portions included in the first detection portion and at least one of the plurality of second detection portions included in the second detection portion are configured as a common detection portion.

8. The fine particle detection device according to claim 1, wherein the first irradiation portion and the second irradiation portion each include an optical waveguide configured to radiate the excitation light to the flow passage.

9. The fine particle detection device according to claim 8, wherein the optical waveguide of the first irradiation portion and the optical waveguide of the second irradiation portion are arranged adjacent to each other in a flow direction of the fine particle in the flow passage.

10. The fine particle detection device according to claim 9, wherein the optical waveguide of the first irradiation portion and the optical waveguide of the second irradiation portion are configured as an integrated optical fiber ribbon.

11. The fine particle detection device according to claim 1, wherein
    the first irradiation portion includes a first optical waveguide configured to transmit third light that has been radiated to the flow passage to the first separation portion, and
    the second irradiation portion includes a second optical waveguide configured to transmit fourth light that has been radiated to the flow passage to the second separation portion.

12. The fine particle detection device according to claim 11, wherein the first optical waveguide of the first irradiation portion and the second optical waveguide of the second irradiation portion are arranged adjacent to each other in a flow direction of the fine particle in the flow passage.

13. The fine particle detection device according to claim 12, wherein the first optical waveguide of the first irradiation portion and the second optical waveguide of the second irradiation portion are configured as an integrated optical fiber ribbon.

* * * * *